United States Patent [19]

Bumol et al.

[11] Patent Number: 5,574,047
[45] Date of Patent: Nov. 12, 1996

[54] METHODS OF INHIBITING IMPERFECT TISSUE REPAIR

[75] Inventors: Thomas F. Bumol, Carmel; George J. Cullinan, Trafalgar, both of Ind.

[73] Assignee: Eli Lilly and Company, Indianapolis, Ind.

[21] Appl. No.: 171,150

[22] Filed: Dec. 21, 1993

[51] Int. Cl.$^6$ ................................................ A61K 31/445
[52] U.S. Cl. ........................ 514/324; 514/317; 514/319; 514/320; 514/443; 514/422
[58] Field of Search .................................. 514/410, 324, 514/317, 319, 320

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 424/267 |
| 5,075,321 | 12/1991 | Schriber | 514/317 |

FOREIGN PATENT DOCUMENTS

| | | |
|---|---|---|
| WO93/10113 | 5/1993 | WIPO. |
| WO93/1074 | 6/1993 | WIPO. |
| PCT/US93/06804 | 2/1994 | WIPO. |

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.
Bryant et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti-estrogen Raloxifene", Am Soc. Bone & Min. Res., Tampa, Sep. 18–22, 1993.
Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.
Sato et al., "DEXA Analysis of Raloxifene Effects on the Bones From Ovariectomized Rats", Am. Soc. for Bone and Min. Res., Tampa, Sep. 18–22, 1993.
Yang et al., "Raloxifene an Anti-Estrogen, Simulates the Effects of Estrogen in Inhibiting Bone Resorption Through Regulating TGFB-3 Expression in Bone;" Am Soc. for Bone and Min. Res., Tampa, Sep. 18–22, 1993.
Black et al., "Distinct, Structure–Related Profiles of Estrogenic and Anti–Estrogenic Activity in the Tamoxifen and LY117018 Series;" the Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.
Black et al., "Differential Interaction of Antiestrogens with Cytosol Estrogen Receptors," Molecular and Cellular Endocrinology, 22:1981, 95–103.
Black et al., "Evidence for Biological Action of the Antiestrogens LY117018 and Tamoxifen by Different Mechanisms," Endocrinology 109;1981, 987–989.
Black, L. J. "Biological Actions and Binding Properites of a New Estrogen Antagosist LY117018," In: Homone Antagonists, 129–82, 1982 (M.K. Agarwal ed.) Walter de Gruyter and Co., Berlin New York.
Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.
Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.
Black et al., Antagonism of Estrogen Action with a New benzothiophene Derived Antiestrogen, Life Sciences, 32:1983. 1031–1036.
Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

(List continued on next page.)

Primary Examiner—Shailendra Kumar
Attorney, Agent, or Firm—James J. Sales

[57] ABSTRACT

A method of inhibiting imperfect tissue repair or a physiological condition due at least in part thereto comprising administering to a human in need thereof an effective amount of a compound having the formula

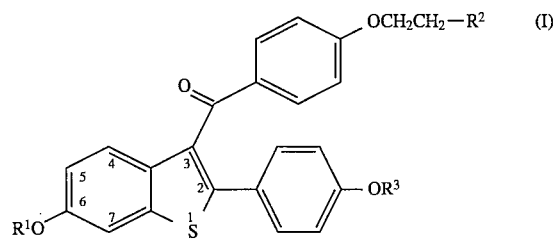

wherein $R^1$ and $R^3$ are independently hydrogen, —CH$_3$,

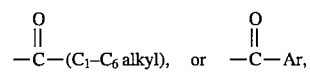

wherein Ar is optionally substituted phenyl;
$R^2$ is selected from the group consisting of pyrrolidine, hexamethyleneamino, and piperidino; or a pharmaceutically acceptable salt of solvate thereof.

5 Claims, No Drawings

OTHER PUBLICATIONS

Black et al., Synthesis and Antiestrogenic Activity of [3,4–Dihydro–2(4–methoxyphenyl)–1–napthalenyl] [4–[2–pyrrolidinyl)ethoxyl]–phenyl] methanone, methanesulfonic acid salt, Journal of Medicinal Chemistry 22; 1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxyl]–phenyl]methanone Hydrochloride (LY156758), a Remarkably Effective Estrogen Antagonist with Only Minimal Intrinsic Estrogenicity, J. Med. Chem. 27(8), 1984, 1057–1066.

METHODS OF INHIBITING IMPERFECT TISSUE REPAIR

BACKGROUND OF THE INVENTION

It has long been known that over the course of an individual's life, one's tissues and organs are subjected to numerous assaults which can compromise their normal function. One of the most important attributes of tissues and organs is their ability to repair damage inflicted on it in order to maintain normal homeostasis. In many circumstances, this repair function is complete and normal function is restored without resulting sequelae. This is often the case when the insult is acute and somewhat mild in nature. However, in other cases, the attempt of a specific tissue to repair the damage inflicted results in either decreased function of the affected tissue and/or an induction of a detrimental effect on another tissue. In acute injury, the imperfect repair leading to a small decrease in tissue function may go unnoticed or be of little consequence, due to the reserve capacity of that tissue to maintain its proper function. In the case of repeated, acute injury, often seen when the injury is caused by external, environmental factors, the small incremental loss of tissue function may be additive. Thus, repeated, acute injury may result in a chronic condition and lead to ultimate failure of the affected tissue or organ. Such repeated, acute injury of various organs are seen with alcohol damage to the liver, infections of the pulmonary tract, exposure to toxins from the environment on the liver, kidney, and pulmonary tract, and the toxic effect of certain drugs, e.g., oncolytic agents, antibiotics, anti-arthritis agents, etc.

In addition to acute and repeated-acute injury, there are many conditions which can be called truly chronic. These conditions may be defined where the injury inflicted on a particular tissue or organ is continuous over a long period of time. Often, the source of chronic injury originates from a condition within the body affecting particular organs and tissues, which may or may not have been directly involved in the originating pathology. This induction of one tissue's pathology into an other tissue's function gives rise to the formation of entire syndromes of various pathologies which are often seen in chronic diseases. Imperfect or inappropriate repair attempts by affected tissues or organs in chronic pathologies may be similar to that seen with acute repair attempts or may be different; however, the results tend to be similar in that there is incremental loss of function which leads to eventual complete or partial failure.

Two examples of chronic conditions which could lead to multi-organ pathologies in which imperfect or inappropriate tissue repair is contributory to eventual organ failure are diabetes mellitus and auto immune diseases, e.g., systemic lupus erythematosus (SLE), rheumatoid arthritis, etc. Chronic pathologies may often be more insidious and less controllable in nature than some of the pathologies associated with acute injury, in that they often are undetected prior to organ failure and often result from originating insults which are poorly understood or which may result at least in part due to a genetic predisposition.

As mentioned before, many pathologies resulting from either acute or chronic insult and subsequent imperfect, ineffective, or inappropriate repair by tissues or organs, are associated with syndromes, i.e., pathologies of many different organs with multiple sequelae. Thus a single causative event can trigger a cascade of events in various body systems. For example, patients suffering from SLE may exhibit pathologies in the kidney, vasculature, lungs, and liver, largely due to one underlying cause (immune complex deposition).

The nature of the imperfect repair is diverse in different tissues and organs and not always well understood. A definition of imperfect, ineffective, or inappropriate repair of damaged tissues or organs is that repair which leads to a loss of normal function of that tissue or organ. Sometimes, this imperfect repair leads to small (focal) lesions which can be compensated by surrounding healthy tissue, thus the tissue may overall function normally in an overall sense. However, if the injuries are repeated or chronic, these incremental decreases in function inexorably lead to total failure and catastrophic results.

Some of the most common examples of imperfect repair seen in many diverse tissues and organs are an increase in fibroid deposition and a proliferation of auxiliary cells at the site of injury. Initially the injury may cause a break in a continuous, fluid carrying system such as blood vessels, arteries, nephron tubules, or air passages. The cause of this break may be mechanical or the loss of normal, interfacing cells or destruction of matrix which forms the system. Whatever the cause, the attempt by the body to repair this break often takes the form of quickly covering the break physically with a wall of cells or matrix components. This physical covering of the break, while temporarily repairing the leakage, does not restore the normal function of the system in that affected area. The repair at the site of the injury usually lacks the biological properties of the original tissue, e.g., the loss of discriminatory filtration properties in the kidney, the loss of structural integrity in arteries and vessels, a loss of permeability in the airways of the lung, etc. Microscopic examinations of these imperfect repair sites often reveal the deposition of fibrin, collagen, and other molecules which lack the biological and/or physical properties of the original matrix which it has replaced. Similarly, there is often a proliferation of auxiliary cells (sometimes referred to as connective tissue cells) which produce more non-functioning, fibroid matrix cells. Lastly, there is often a proliferation of the normal and functional cells of the particular tissue; however, the proliferation, while beneficial in number, may be ineffective in total function due to the disruption of critical architecture. Thus, the overall loss of either chemically or biologically important matrix, loss of functional cells by replacement of repair cells, or a loss of critical architecture of functioning cells leads to the failure of the tissue or organ to perform its homeostatic function.

Additionally, there are often inappropriate responses to injury and repair. Prime examples are an immune-inflammatory or inflammatory responses at the site of injury. Although these responses are beneficial and critical to protect the body from many insults such as bacteria, viruses, or external pathogens, or are beneficial in removing dead or malfunctioning cells or matrix in normal circumstances, these responses can be inappropriately triggered or become out of control at repair sites. In some cases, an inappropriate response of certain cells may be causal to further damage as well as being detrimental to the repair. For example, in auto-immune diseases, immune diseases, immune complex deposition in various tissues and organs may cause local inflammation and damage, triggering a repair response and simultaneously causing the repair to be imperfect or ineffective.

A method of inhibiting imperfect tissue repair and physiological or pathological conditions caused at least in part thereby would be beneficical.

SUMMARY OF THE INVENTION

This invention provides methods for inhibiting imperfect tissue repair comprising administering to a human in need thereof an effective amount of a compound of formula I

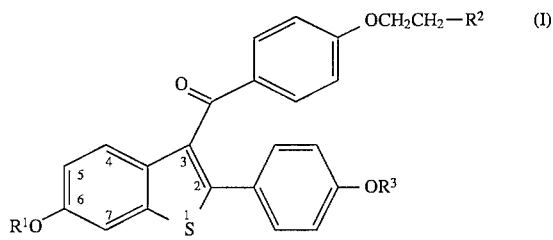

wherein $R^1$ and $R^3$ are independently hydrogen, $-CH_3$,

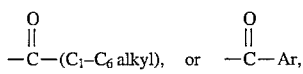

wherein Ar is optionally substituted phenyl;

$R^2$ is selected from the group consisting of pyrrolidino, hexamethyleneimino, and piperidino; and pharmaceutically acceptable salts and solvates thereof.

Raloxifene, (the hydrochloride salt of a compound of formula 1, wherein $R^1$ and $R^3$ are hydrogen, and $R^2$ is 1-piperidinyl), and selected analogs are useful in the treatment of the syndromes associated with the imperfect, ineffective, or inappropriate repair of body tissues or organs resulting from acute, repeated acute, or chronic injury and are the subject of this invention.

DETAILED DESCRIPTION OF THE INVENTION

The current invention concerns the discovery that a select group of 2-phenyl-3-aroylbenzothiophenes (benzothiophenes), those of formula I, are useful for inhibiting imperfect tissue repair. The methods of treatment provided by this invention are practiced by administering to a human in need thereof a dose of a compound of formula I or a pharmaceutically acceptable salt or solvate thereof, that is effective to inhibit imperfect tissue repair.

The term "inhibit" is defined to include its generally accepted meaning which includes preventing, prohibiting, restraining, and slowing, stopping or reversing progression, or severity, and holding in check and/or treating existing characteristics. As such, the present method includes both medical therapeutic and/or prophylactic administrations, as appropriate.

The term "imperfect tissue repair" includes ineffective, inappropriate or inadequate tissue repair due to, at least in part, an insult to the tissue. The insult may be acute, repeated-acute or chronic, and includes inappropriate immune-inflammatory response, and results in loss of normal function of the tissue or organ.

Physiological conditions caused by or associated with imperfect tissue repair include those conditions which are due, at least in part, to the imperfect repair and therefor can be said to be a symptom of the imperfect tissue repair.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418, 068, and 4,380,635 all of which are incorporated by reference herein. In general, the process starts with a benzo[b] thiophene having a 6-hydroxyl group and a 2-(4-hydroxyphenyl) group. The starting compound is protected, alkylated or acylated, and deprotected to form the formula I compounds. Examples of the preparation of such compounds are provided in the U.S. patents discussed above. Optionally substituted phenyl includes phenyl and phenyl substituted once or twice with $C_1-C_6$ alkyl, $C_1-C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit imperfect tissue repair or physiological conditions due at least in part thereby, according to this invention, will depend upon the severity of the condition, the route of administration, and related factors that will be decided by the attending physician. Generally, accepted and effective daily doses will be from about 0.1 to about 1000 mg/day, and more typically from about 50 to about 600 mg/day. Such dosages will be administered to a subject in need of treatment from once to about three times each day, or more often as needed.

It is usually preferred to administer a compound of formula I in the form of an acid addition salt, as is customary in the administration of pharmaceuticals bearing a basic group, such as the piperidino ring. It is also advantageous to administer such a compound by the oral route. For such purposes the following oral dosage forms are available.

Formulations

In the formulations which follow, "active ingredient" means a compound of formula I.

Formulation 1: Gelatin Capsules
Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2: Raloxifene capsule

| Ingredient | Quantity (mg/capsule) |
|---|---|
| Raloxifene | 1 |
| Starch, NF | 112 |
| Starch flowable powder | 225.3 |
| Silicone fluid 350 centistokes | 1.7 |

Formulation 3: Raloxifene capsule

| Ingredient | Quantity (mg/capsule) |
|---|---|
| Raloxifene | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
|---|---|
| Raloxifene | 10 |
| Starch, NF | 103 |
| Starch flowable powder | 225.3 |
| Silicone fluid 350 centistokes | 1.7 |

Formulation 5: Raloxifene capsule

| Ingredient | Quantity (mg/capsule) |
|---|---|
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
|---|---|
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |

Formulation 7: Tablets

| Ingredient | Quantity (mg/tablet) |
| --- | --- |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Falvor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

For topical administration, the compounds may be formulated as is known in the art for direct application to an area. Conventional forms for this purpose include ointments, lotions, pastes, jellies, sprays, and aerosols. The percent by weight of a compound of the invention present in a topical formulation will depend on various factors, but generally will be from 0.5% to 95% of the total weight of the formulation, and typically 1–25% by weight.

The compositions can take the form of an aqueous or anhydrous solution or dispersion, or alternatively the form of an emulsion or suspension.

These compositions can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carob gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colourings.

Also, other active ingredients may be added, whether for the conditions described or some other condition.

For example, among antioxidants, t-butylhydroquinone, butylated hydroxyanisole, butylated hydroxytoluene and α-tocophrol and its derivatives may be mentioned. The galenical forms chiefly conditioned for topical application take the form of creams, milks, gels, dispersions or microemulsions, lotions thickened to a greater or lesser extent, impregnated pads, ointments or sticks, or alternatively the form of aerosol formulations in spray or foam form or alternatively in the form of a cake of soap.

The following topical compositions are prepared:

Formulation 9

| Ingredient | Quantity (mg/5 ml) |
| --- | --- |
| Hydroxypropylcellulose | 1.5 g |
| Active ingredient | 1.5–30 g |
| Isopropanol qs | 100 g |

Formulation 10

| Ingredient | Quantity (mg/5 ml) |
| --- | --- |
| Hydroxypropylcellulose | 1.5 g |
| Ethyl lactate | 15.0 g |
| Active ingredient | 1.5–30 g |
| Isopropanol qs | 100 g |

Formulation 11

| Ingredient | Quantity (mg/5 ml) |
| --- | --- |
| Hydroxypropylcellulose | 1.0 g |
| Butylated hydroxytoluene | 0.02 g |
| Active ingredient | 1.5–25 g |
| Ethanol qs | 100 g |

Formulation 12

| Ingredient | Quantity (mg/5 ml) |
| --- | --- |
| Hydroxypropylcellulose | 1.5 g |
| Butylated hydroxytoluene | 0.01 g |
| $C_8$–$C_{12}$ fatty acid triglycerides | 10.0 g |
| Active ingredient | 1.5–30 g |
| Isopropanol qs | 100 g |

Formulations 9–12 take the form of gels.

Formulation 13

| Ingredient | Quantity (mg/5 ml) |
| --- | --- |
| Isopropanol | 46.0 g |
| Active ingredient | 1.0–15 g |
| $C_8$–$C_{12}$ fatty acid triglycerides | 49.0 g |

Formulation 14

| Ingredient | Quantity (mg/5 ml) |
| --- | --- |
| Ethanol | 69.0 g |
| Ethyl lactate | 10.0 g |
| Active ingredient | 1.5–20 g |

-continued

Formulation 14

| Ingredient | Quantity (mg/5 ml) |
|---|---|
| $C_8$–$C_{12}$ fatty acid triglycerides | 30.0 g |

Formulation 15

| Ingredient | Quantity (mg/5 ml) |
|---|---|
| Isopropanol | 47.0 g |
| Acetone | 10.0 g |
| Ethyl lactate | 10.0 g |
| Active ingredient | 1–15 g |
| $C_8$–$C_{12}$ fatty acid triglycerides | 30.0 g |

Formulation 16

| Ingredient | Quantity (mg/5 ml) |
|---|---|
| Ethanol | 95.08 g |
| Butylated hydroxytoluene | 0.02 g |
| Active ingredient | 1.5–2.5 g |

Formulations 13, 14, 15, and 16 take the form of lotions.

Formulation 17

| Ingredient | Quantity (mg/5 ml) |
|---|---|
| White vaseline | 50.0 g |
| Liquid paraffin | 15.0 g |
| Refined paraffin wax | 32.0 g |
| Active ingredient | 1–20 g |

Formulation 18

| Ingredient | Quantity (mg/5 ml) |
|---|---|
| White vaseline | 50.0 g |
| Liquid paraffin | 13.0 g |
| Refined paraffin wax | 32.0 g |
| Active ingredient | 1–20 g |

Formulations 17 and 18 take the form of sticks.

Illustrations of the use of this invention will focus on conditions and pathologies effecting kidney, liver, vascular, and pulmonary function; however, this invention is in no way limited to these indications. In many cases due to the observation of an increase in fibrous matrix, many conditions are referred to in the art as fibrosis or fibrotic states, and this invention is not limited solely to pathologies or physiological conditions so named.

I. PATHOLOGIES OF THE KIDNEY

A. NEPHROTIC SYNDROME (NS)

The most general, clinical characteristics seen with patients suffering from NS are: albuminuria, hypoalbuminemia, hyperlipidemia, and edema. These abnormal clinical findings are the direct or indirect result of abnormal leakage of serum proteins into the urine and subsequent loss by excretion (proteinuria). Simplisticly this leakage and loss of serum proteins can be called a loss of the glomerular appartratus to selectively filter elements of the serum for excretion in urine; however, the actual mechanisms of this loss in filtration selectivity are diverse and complicated. These pathologies by which filtration failure occur are listed below and are connected with imperfect repair of damage inflicted, primarily on the epithelium of the glomerular apparatus.

The sequelae resulting from the loss of various serum proteins are numerous and serious. They are examples of the induction of pathology into other organs and tissues by an apparently unrelated failure in the kidney.

One of the major proteins lost in NS is albumin. The loss of albumin in the serum leads to a decrease in plasma oncotic pressure and has a negative impact on the Starling forces acting across the peripheral capillaries. The decrease in oncotic pressure and the imbalance of the Starling forces causes water to flow from the circulation into the interstitial tissues, especially in areas of low tissue pressure. This buildup of water in these tissues leads to an edematous state, causing decreased efficiency and/or failure of that tissue to function. Additionally, due to the lower effective volume of the plasma, the rennin-angiotensin-aldosterone system is activated leading to retention of salt and water, thus perpetuating the edematous state. Common sites affected by edema are the lungs and extremities. Edema is often associated with certain types of cardiovascular and pulmonary insufficiency and collapse. Current therapy for the treatment of edema of this origin are inadequate, and they include furosemide, ethacrynic acid and other loop diuretics and administration of salt-poor albumin. These treatments run the risk of causing acute renal failure or severe hypotension.

Another major sequelae of albumin loss is the inappropriate response of the liver to boast levels of LDL and cholesterol to compensate. This elevation of LDL and cholesterol can lead to an increase in atherosclerosis and other vascular diseases. Treatment with conventional lipid lowering agents for this aspect of NS is often not satisfactory due the compromise of renal function and subsequent toxicity of the therapy.

The loss of other serum proteins has other associated pathologies. For example, the loss of major quantities of transferrin can lead to certain types of anemia; the loss metal binding proteins leads to metabolic abnormalities; the loss of IgG leads to an increase in susceptibility to infectious agents; the loss of T4 leads to metabolic abnormalities; loss of cholecaciferol-binding protein leads to vitamin D deficiency, secondary hyperthyroidism, bone disease, and be contributory to hypocalcemia and hypocalciuria.

Another serious pathology associated with protein loss is thrombosis. The greater loss of antithrombin III relative to the pro-coagulating proteins may lead to a hypercoagulable state. Thrombosis and blockage of the vasculature to critical organs, especially the heart, lungs and kidney, are most serious.

Currently, there are numerous treatments for many of these conditions with various degrees of effectiveness; however, the situation can be further complicated by the fact that many useful drugs are carried by albumin in the circulation, thus reduction of albumin in NS changes the pharmacokinetics of these drugs making it difficult to manage the pathologies. Clearly, when dealing with such a cascade of events seen in NS, it would be useful to treat NS at the source of the problem, i.e., normalize the filtration selectivity in the kidney.

The primary cause of NS is primary glomerular disease (Idiopathic Nephrotic Syndrome). Primary glomerular disease is further classified into four main types: Minimal Change Disease (lipoid nephorosis, nil lesion, foot process disease); Focal and Segmental Glomerulosclerosis (focal sclerosis); Membranous Glomerulopathy; and Proliferative Glomerulonephritis (Membranoproliferative Glomerulonephritis, Cresentic Glomerulonephritis, "Pure" Mesangial Proliferative Glomerulonephritis, Focal and Segmental Proliferative Glomerulonephritis).

There are many conditions and diseases which cause NS in a secondary manner. These conditions and diseases inflict damage to the kidney which can be acute, repeated-acute, or chronic in nature: Infectious agents (Strepoococcal, infectious endocarditis, secondary syphilis, sepsis, leprosy, hepatitis B, mononucleosis, malaria, schistosomiasis, pneumoccal, mycoplasma, staphylococcal, and filariasis); Drug Toxicity (heroin abuse, probenicid, tridione, contrast media, anti-venoms and toxins, arthritis drugs-gold and penicillamine); Neoplastic Diseases (Hodgkin's, lymphomas, leukemias, carcinomas, melanoma, Wilm's tumor); Environmental toxins (natural or unnatural, such as mercury); or Multisystem Diseases (SLE, Schonlein-Henoch purpura, vasculitis, Goodpasture's Syndrome, dermatomyositis, amyloidosis, sarcoidosis, rheumatoid arthritis, Sjogren's Syndrome); Heredofamilial Diseases (diabetes mellitus, Alport's Syndrome, sickle-cell, Farbry's Disease); Other Diseases (Berger's Syndrome, thyroiditis, myxedema, malignant obesity, renovascular hypertension, chronic allograft rejection, bee stings).

The pathogenesis of each of the four major causes of NS are listed below. A central or contributing pathological event seen with most of these causes is an imperfect attempt to repair an injury which has lead to some type of non-functional properties of that repair or a loss of critical architecture.

1) Minimal Change Disease(MCD)

The pathogenesis and etiology of this disease is not known and cause of injury to the glomerular apparatus is not known. However, there is a profound loss of architecture in foot processes of the epithelial cells (podocytes). It is not clear whether this particular cause of NS is due to a repair fault or a failure in the function of the podocyte. Treatment of this disease often includes glucocorticoids, cylcophosphamide and chlorambucil, anti-proliferative and anti-inflammatory drugs, which are dangerous when used for prolonged periods of time.

2) Focal and Segmental Glomerulosclerosis (Focal Sclerosis)

In this disease, one cause of injury is thought to be IgM complex deposition and C3 (complement factor III, a possible inflammatory substance) involvement. The tissue response is, again as in MCD, a loss of architecture of the podocytes and hyalinization of the glomeruli, a malfunction in matrix production. There is no effective treatment for this disease.

3) Membranous Glomerulopathy

In this disease, causes are known to be: IgG deposition, some infectious agents, tumors, heavy metals, or certain drugs. The resulting injury leads to discontinuous proteinaceous deposits on the subepithial aspect of the glomerular capillary wall, increased amounts and thickening of the basement membrane, all matrix defects. Treatment of this disease is limited to the use of glucocorticoids and this treatment is controversial as to its effectiveness.

4) Membranoproliferative Glomerulonephritis

This group of diseases has a common pathology of proliferation of mesangial cells and an increased synthesis of matrix. This response leads to the destruction of critical architecture and membrane selectivity and function. The cause of injury is due at least in part to Ig deposition. Treatment for this disease with glucocortocoid steroids may delay the progression of the disease, but is not satisfactory. Kidney transplants are also used to treat the disease; however, the prognosis is poor.

B. ACUTE GLOMERULONEPHRITIS (AGN)

AGN is characterized by rapid onset of proteinuria, hematuria, azotemia (insufficency of glomerular filteration rate), and salt and water retention. The major pathological sequelae induced by AGN are edema, circulatory congestion, and arterial diastolic hypertension. These pathologies can lead to failure of the lungs and cadiovascular system. As the name implies, this condition is acute in nature and often quickly is resolved without extensive intervention; however, it can be most serious and lead to NS or chronic nephritis. The causes of AGN can be: infectious diseases- poststreptococcal glomerulonephritis, endocarditis, sepsis, pneumococcal pneumonia, typhoid fever, secondary syphilis, meningococcemia, hepatitis B, mononucleosis, mumps, measles, vaccinia, echovirus, and coxsackievirus; multisystem disease- SLE, vasculitis, Schonlein-Henoch purpura, Goodpasture's syndrome; primary glomerular disease; and other sources such as serum sickness.

The pathogenesis of AGN is somewhat different from NS and poorly understood; however, it often has lesions and similarities which suggest an imperfect response to an injury has occurred as seen in NS. Currently, the treatment of AGN with glucocorticoids is of questionable benefit. It would seem reasonable that a therapy for NS would be of use in some aspects of AGN.

C. RAPIDLY PROGRESSIVE GLOMERULONEPHRITIS (RPGN)

RPGN is similar to AGN with the exception that it rapidly leads to renal failure in a matter of weeks or months. The resulting sequelae are similar to those in AGN. The pathogenesis clearly shows extensive extra capillary cellular proliferation and destruction of architecture with "crescent" formation. Additionally, there is fibrin polymerization and focal discontinuities in the glomerular basement membranes. Treatment is supportive and insufficient. Agents which normalize epithelial proliferation and matrix production would be useful in this condition.

D. CHRONIC GLOMERULONEPHRITIS (CGN)

As the name suggests, this condition is characterized by persistent abnormalities and slow progressive loss of renal function. The most troublesome sequelae of CGN is hypertension and cardiovascular collapse. Cause of the disease is usually the protracted presence of NS. Its pathogenesis is marked by cellular proliferation, sclerosing, and membrane and matrix abnormalities. Treatment is supportive and effectiveness is unsatisfactory. An agent which would normalize cellular proliferation and membrane-matrix function would be useful to treat CGN.

II. PATHOLOGIES OF THE LIVER

Cirrhosis of the liver is a serious pathology which involves the attempt of liver tissue to repair damage inflicted on it. Cirrhosis is often the end stage of many diseases which effect the liver and leads to hepatic insufficiency and failure. Cirrhosis, like nephrotic syndrome, shows the hallmarks of imperfect repair processes involving matrix, proliferative cellular, and architectual faults. Also, in many cases, an inappropriate inflammatory response is seen at the repair site, which can lead to further damage.

Cirrhosis, a general term, includes all forms of chronic diffuse liver diseases characterized by loss of hepatocytes, disorganization and fibrosis of the retculin network, disorganization of the vascular bed, and disorganization of the regenerating hepatocytes into nodules in the fibrous matrix. The precipitating event (damage) in cirrhosis is usually diffuse cell death from a number of causes listed below. The morphological changes induced by the attempt to repair this damage are wide spread and have serious consequences. For example, loss of functional hepatocytes leads to the sydrome of hepatic insufficiency- jaundice, central nervous system dysfunction (hepatic encephalopathy, coma), edema and ascites, and cachexia. Disorganization and distortion of the vascular and lymphatic beds can lead to portal hepatic hypertension and splenomegaly.

There are four major conditions recognized to precipitate the damage leading to cirrhosis of the liver:

1) Alcoholic Liver Disease and Cirrhosis

Alcoholic liver disease refers to a spectrum of liver injury and can be associated with acute, repeated acute, chronic alcoholism. There are three major components of this disease: fatty liver, alcoholic hepatitis, and alcoholic cirrhosis. All three may found in the same patient and may be independent of each other. Alcoholic cirrhosis is characterized by scarring, loss of hepatocytes, and nodular regeneration. At sites of damage there can be found fibroblasts (connective tissue cells) and collagen matrix. Alcoholic cirrhosis has also been called Laennec's, micronodular, portal, or fatty cirrhosis.

Treatment of alcoholic cirrhosis is supportive to the induced sequelae. Treatment of the dysfunctional liver is insufficient, but includes abstainance from alcohol and glucocorticoids.

2) Postnecrotic Cirrhosis

Postnecrotic cirrhosis is the most common type of cirrhosis and is marked by: extensive loss of hepatocytes, collapse of the stromal matrix and fibrosis producing large bands of connective tissue, and irregular nodules of regenerating cells, i.e., a condition of precipitating damage by cell death followed by a repair process which destroys the functional matrix and disorganizes architecture. Adding to the imperfect repair of the hepatic damage, there is often seen an inappropriate infilteration of imflammatory mononuclear cells which may cause further damage. Postnecrotic cirrhosis is also known in the art as toxic cirrhosis, coarsely nodular cirrhosis, posthepatic cirrhosis, cryptogenic cirrhosis, and multilobular cirrhosis.

The etiology of postnecrotic cirrhosis is not well understood; however, there is serologic evidence that viral hepatitis may be a common antecedent, especially Hepatitis B and non A-non B Hepatitis. Other pathologies leading to postnecrotic cirrhosis are: chemical toxins, e.g., phosphorous; toxins, e.g., *Amantia phalloides*; infections, e.g., brucellosis; parasitic infections, e.g., clonorchiasis; and advanced alcoholic liver disease. Additionally, patients with chronic active hepatitis (stemming from viral infection) may progress to postnecrotic cirrhosis.

Major sequelae of postnecrotic cirrhosis are similar to other types of cirrhosis, especially jaundice, ascites, abdomimal pain, hepatic encephalopathy, and portal hypertension. Treatment is supportive and treatment for underlying damage-repair pathology is not available.

3. Biliary Cirrhosis

The pathogensis and morphology is similar to postnecrotic cirrhosis, only the major lesions effect the bile ducts to a greater degree. The etiology of this condition is not known; however, since it is a disease of middle-aged women, there is a strong possiblity that it has an endocrine component.

Due to the blockage of the bile ducts and subsequent accumulation of bile products, the major sequelae are markedly different from other forms of cirrhosis. Often seen are: dark urine, itching of the skin, xanthelasmas of the joints and skin, hyperpigmentation, hyperlipidemia and malabsorption of lipid soluble vitamins. The malabsorption of vitamins A, K and D lead to osteomalacia, diarrhea, and purpura. Death is often caused by variceal hemorage, hepatic insufficiency, infection, and surgical attempts to open the bile ducts.

Treatment is either supportive or surgical proceedure, and there is no treatment for the underlying liver pathology.

4) Cardiac Cirrhosis

Cardiac cirrhosis is caused by chronic, severe right-sided congestive heart failure. This circulation failure precipitates hepatocyte necrosis and triggers the cirrhotic cascade. The only available treatment for cardiac cirrhosis is to correct the cardiac failure, if possible.

III. PATHOLOGIES OF THE CARDIO-VASCULAR SYSTEM

Arteriosclerosis is a general term for the thickening and hardening of the arterial wall. Atherosclerosis is a patchy nodular type of arteriosclerosis. The thickening of the arterial wall through the development of atherosclerotic plaque leads initially to restricted blood flow. A fissure or crack in this plaque initiates the development of a thrombus or clot which leads to tissue ischemia. If unresolved, the thrombus could lead to tissue and organ failure and possibly death. Examples of arterial thrombotic events include stroke, myocardial infarction and peripheral vascular diseases. Atherosclerosis is the underlying basis for cardiovascular disease being the leading cause of death and morbidity in the United States.

There are three types of lesions found in the arteries which are associated with atherosclerosis: fatty streaks, fibrous plaques, and complicated plaques. Fatty streaks occur early in life and consist of an accumulation of lipid filled macrophages (foam cells) and accumulated fibrous tissue on the intima. In general, these fatty streaks appear not to be particularly dangerous in themselves; however, they may be contributary to the formation of fibrous plaques. Fibrous plaques are raised lesions on the intima. These plaques consist of a central core of extracellular lipid and necrotic cell debris and covered with an overlayment of smooth muscle cells and collagen rich extracellular matrix. This makes the fibrous plaque foci, a place of constricted blood flow in the artery. The fibrous plaque is characteristic of advancing atherosclerotic disease. The complicated plaque is a calcified fibrous plaque and is an area of thrombosis, necrosis, and ulceration. This plaque can be the site of exclusive thrombosis which constricts the blood flow and cause stenosis and organ insufficiency. The site of a complicated plaque can also be an area of weakened arterial wall which can fail causing an anerurysm or hemorrhage.

One theory on the development of atherosclerosis is termed the "response to injury" hypothesis. According to this hypothesis, the vascular endothelial cells lining the artery are exposed to acute, repeated acute or chronic injury leading to endothelial cell dysfunction and in some cases cellular death, exposing the underlying medial and connective tissue beds. This break in the continuous system of endothelium can elicit platelet adhesion and aggregation with the formation of microthrombi. These events can cause the release of factors which can stimulate cellular proliferation, cellular migration and the production of extracellular matrix compounds all of which can contribute to an abnormal repair process. Although this repair corrects the immediate break in the system, repeated insults over a long period of time can lead to the development of atherosclerotic plaque at the site providing an example of imperfect, ineffective or inappropriate repair of a tissue in response to an initiating injury.

There are many risk factors which contribute to this atherogenic response, which include: hyperlipidemia (hypercholesterolemea and triglyceridemia), hypertension, cigarette smoking, hyperglycemia and diabetes mellitus, obesity, a sedentary lifestyle, stress, and family history of cardiovascular diseases. The current treatment of atherosclerotic disease is limited to cholesterol and triglyceride lowering drugs to modulate hyperlipidemia as well as many therapies designed to address thrombosis associated with atherosclerosis (i.e. aspirin). Lifestyle changes to eliminate contributing risk factors for vascular injury are also prescribed. There are no current therapies which address the defective repair process.

IV. PATHOLOGIES OF THE LUNG

The general term "infiltrative" means the diffusion into and accumulation in a tissue of those substances which are either foreign to it or endogenous substances which inhibit normal function. For example, infections (bacterial pneumonias) elicit immune or inflammatory cells into the interalveolar space or the invasive spread of neoplastic cells into the lung, these are foreign cells to the normal lung structure. In other cases endogenous substances such as hyaline membrane, fibrous matrix, and proliferation of normal alveolar and bronchial epithelial cells accumulate in the intraalvveolar space leading to a dysfunctional foci in the lung.

In most cases, the lung is able to repair itself without lasting detrimental sequelae; however, if the injury is repeated acute or chronic in nature, the progressive number of non-functioning lesions (imperfect, ineffective, or inappropriate repair) begins to affect an insufficiency in pulmonary function. The pathogensis in this disease is very similar to the pathogenesis described for the liver, kidneys and vascular wall. As in the case of liver and kidney, the primary tissue which responds to the damage is the epithelium. The response of the epithelium is to quickly repair the damage to the alveolar-capillary interface with the production of fibrous matrix (collagen and hyaline membrane) and hyperplastic expansion of cells. This new structure, while restoring the barrier between the air (alveolar) and circulatory (capillary) spaces, is not able to selectively mediate the exchange of gases with the same effectivenes as the normal tissue.

The major sequelae of the accumulated loss and insufficiency of the lung is hypoxia of critical organs and their failure.

The initiating or antecedent pathologies of diffuse infiltrative lung disease are numerous and are listed in abrieviated form: Infections such as viral (influenza, CMV, etc.) bacterial (mycoplasma, streptococcal, staphylococcal, etc.) parasitic (schistosomiasis, *Pneumocstis carinii*, filariasis, etc.) fungal (histoplasmosis, candidis, etc.); Occupational causes such as mineral dusts and chemical fumes; Neoplasms; Congenital and familial pathologies such as cystic fibrosis; Metabolic diseases such as uremic pneumonitis and hypercalcemia; Physical trauma; Circulatory diseases such as thromboembolic and pulmonary edema; Immunological diseases such as hypersensitivity pneumonia; and Collagen diseases such as scleroderma, rheumatoid arthritis, SLE, etc.

Treatment of diffuse infiltrative lung disease is supportive treatment of the induced hypoxic complications and treatment of the initiating diseases. The treatment of the faulty repair process itself is mostly confined to the administration of corticosteroids, which in many cases are only partially effective and care must be taken not to induced the undersirable effects of the steroids.

V. PATHOLOGIES CAUSED BY THE REPAIR RESPONSE TO INFLAMMATORY DAMAGE

Inflammation is an important and beneficial response by the body to destroy invading pathogens (via the immune system) and scavenge dead or non-functional tissues or debris from the body. However, in some circumstances, this system becomes uncontrolled and the inflammatory process damages normal tissue. This damage can lead to an imperfect repair response. Often, this faulty repair response further initiates the inflammation and a vicious cycle is established leading to greater and greater dysfunction. Several examples of this chronic destructive cycle have been illustrated above. Further examples of instances where inflammatory initiated disease elicits imperfect repair response are: muscular dystrophies, scleroderma, and Crohn's Disease of the colon.

Raloxifene and selected analogs are useful in treating the imperfect repair of tissue and organs damaged by inflammation and is also a subject of this invention.

ASSAYS

Assay I

Between three and twenty patients suffering from diseases which are causing increasing symptoms of nephrotic syndrome are selected for clinical evaluation. The selection criterion for these patients are 1) preferably post-menopausal women, 2) patients suffering from diseases which often include the induction of nephrotic syndrome as part of the disease pathology, e.g., diabetes mellitus, hepatitis B, Sjogren's patients taking gold for rheumatoid arthritis, etc., 3) patients exhibiting a progressive increase in proteinuria, hypoalbuminemia, hyperlipidemia and edema. These patients are put on a protocol of 50–600 mg of a compound of formula I given by oral administration as a daily single or split dose. These patients continue this protocol for up to twelve months and at appropriate intervals, are evaluated as to the status of the progression of their proteinuria, hypoalbuminemia, hyperlipidemia or edema. A positive impact in this assay would be the slowing or reversing of the progression of these parameters.

Assay II

Between three and fifty patients suffering from diseases known to induce nephrotic syndrome or taking medications known to produce nephrotic syndrome are selected. The selection criterion for these patients is 1) preferably post-menopausal women, and 2) patients, which at the time of entry into the clinical trial, do not as yet demonstrate signs of nephrotic syndrome. Such patients might be women, 45–55 years of age, suffering from diabetes mellitus, but as yet show no signs of diabetic complications involving kidney function. Half of these patients are given a placebo. The other half are enrolled in a regiment of 50–600 mg of a compound of formula 1 given by oral administration per day as a single or split dose. This protocol continues for 1–5 years. A positive impact in this assay would be that, at the end of the trial period, the drug treated group will have fewer cases of pathologies associated with nephrotic syndrome, e.g., hyperlipidemia, proteinuria, hypoalbuminemia, or edema.

Assay III

Puromycin aminonucleoside (PA) nephrosis in the rat is a well-defined model of renal injury/repair ("Toxicology of the Kidney", ed. by J. B. Hook and R. S. Goldstein, Raven Press Ltd., New York, 1993). PA induces a nephrotic syndrome with selective proteinuria, hypoalbuminemia, and high plasma cholesterol. During the early stages of disease, glomerular filtration rate is also depressed. The model shares many clinical and morphological findings with human minimal change glomerulopathy and focal segmental glomerulosclerosis. Extracellular matrix (ECM) synthesis, deposition and organization are prominent in this injury/repair model and studies are initiated to probe this models possible utility for identifying agents which can positively effect tissue repair.

PA (6-dimethylaminopurine, 3-amino-d-ribose) is a purine antagonist with antibiotic activity. The drug inhibits protein synthesis by acting on the RNA synthesis at the level of the ribosome. In this model, proteinuria starts at 5 to 7 days after a single intravenous injection of 50 to 100 mg PA/kg body weight. The proteinuria reaches peak values averaging 300–900 mg/24 hr after 8 to 12 days, and dissipates within 3 weeks. Histological examination can detect moderate swelling of the glomerular visceral epithelial cells. When proteinuria ensues, these changes are accompanied by focal loss of covering epithelium outside the glomerular basement membrane.

Several investigators (Diamond et al., *Kidney Intl.*, 33:917 (1988)) have speculated that certain histological features of focal and segmental glomerulonephrosis (FSGS) also resemble the lesion of atherosclerosis and may indicate a similar pathogenesis. In atherogenesis, the arterial intimal tissue thickens and is composed of vascular smooth muscle cells (VSMC), elastic and collagen fibers, and glycosaminoglycans lying beneath the endothelium. These thickened intimal regions contain isolated macrophage foam cells, and eventually, lipid-filled VSMC, and finally foci of necrosis appear. The similarities of FSCG includes; mesangial expansion with mesangial cell (MC) proliferation, mesangial foam cell accumulation, deposits of amorphous debris, necrosis of tissue, and eventual sclerosis. Glomerular MC and VSMC are closely related in terms of origin, microscopic anatomy, histochemistry, and contractility.

Acute 14 Day Renal Injury Model:

Ovariectomized female Sprague Dawley rats are used, 200 to 250 gms. The animals are housed in metabolic cages for the duration of the experiment with collection of the urine every 24 hours for the measurement of total urinary protein concentration and renal excretion volume.

The rats are initialy anesthetized with ketamine/Rompun [Xylazine] (0.2 ml of a 1:2 mixture, i.m.) and are given an iv. injection of puromycin aminonucleoside (PA), [75 mg/kg, Sigma lot#90H4034] administered in 2.9 ml of saline over a 5 minute period in the tail vein using a HARVARD compact infusion pump equipped with a 5 ml syringe at a pump setting of 9 ( approx. 2.9 ml/5 min.). The animals are dosed P.O. beginning DAY 0 to DAY 13 with a compound of formula 1 or 17 a-Ethynylestradiol (Sigma, E-4876, lot#112H0765) in 20% cyclodextrin.

Urine Protein Assay:

Urine volumes from each rat are recorded daily and a 1 ml. sample is collected and frozen. The Pierce BCA protein assay is selected to determine the protein concentration of the urine. This method is highly sensitive for the spectrophotometric determination of protein concentration. A standard curve is prepared by diluting a BSA standard solution (1 mg/ml, Pierce) with Dulbecco's Phosphate Buffered Saline (D-PBS) (Gibco). Using a multichannel piper, the standard is diluted 1:2 down a Falcon 3911 Micro Test III flexible 96 well assay plate in duplicate wells, ending in a final concentration of 7.81 ug/ml.

Urine samples are thawed and a starting dilution of 1:5 is made in the Falcon plates using D-PBS. Samples are set-up in duplicate wells and resuspended 1:2 down the plate. Seven dilutions are made ending in a final dilution of 1:320. 10 ul of each diluted sample is removed from the Falcon microtiter plate using a multi-channel pipetter and added to a Immulon 2 flat bottom plate for developing and reading purposes.

A protein working reagent is prepared by combining 50 parts of BCA reagent A with 1 part of BCA reagent B (provided in the Pierce Assay Kit). 200 ul of working reagent is added to each well of the Immulon plate. The plates are covered and wrapped in aluminum foil and incubated at 60° C. for 30 minutes.

The plates are read on a Bio-Tek microplate autoreader interfaced with a Macintosh SE/30 personal computer at an absorbance of 570 nm. Data is obtained and calculated using the Delta Soft Elisa Analysis version 2.9B software provided by Bio-Tek Instruments.

Histology—GN Scores:

On day 14, the animals are bled from the orbital sinus, sacrificed by $CO_2$ administration and the kidneys are removed, and processed for histological analysis. After 24 hour fixation, the kidneys are processed and embedded in paraffin. Cross-sections of each kidney (aprox. 3u) are cut, stained with hematoxylin and eosin and 30 glomeruli/rat are scored according to the following criteria: (1+) <25% of the glomerulus affected; minimal damage; little or no matrix expansion. (2+) 25–50% affected; moderate damage; substantial increase or decrease in cellularity; capsule/tuft adhesions may be present; some capillary lumina collapse; thickened basement membranes; protein droplets may be found in the capsule. (3+) 51–75% affected; substantial damage; further increase in mesangial matrix; sclerosis; extensive collapse of capillary lumina with trapping of amorphous material. (4+) 76–100% affected; severe destruction; in most cases the glomerulus appears non-functional or necrotic; extensive sclerosis or lysis.

Crescent formation (defined as four or more contiguous epithelial cells of bowman's capsule) increases the score by 1+. A total score per kidney is determined by multiplying the degree of damage (1+ to 4+) by the percentage of the glomeruli with the same degree of injury, and then adding these scores together. The final GN score is obtained by the addition of the two kidney scores.

PCNA immunohistochemisty and proliferating cell index (PCI)

Identification of proliferating cell nuclear antigen (PCNA) positive proliferating cells is performed using a monoclonal mouse anti-PCNA antibody (Chemicon, #MAB424) and a biotin-streptavidin-horseradish peroxidase labeling system (KPL#710018) with diaminobenzidine as a chromogen. The PCI is determined by counting the number of positive cells/glomerulus in each of 30 glomeruli per kidney and then calculating the mean PCI/rat. No distinction is made between mesangial, endothelial or epithelial proliferating cell types.

Activity of compounds of formula 1 is illustrated by the amelioration of kidney damage or an indication of such, as determined above.

We claim:

1. A method of inhibiting imperfect tissue repair comprising administering to a human in need thereof an effective amount of a compound having the formula

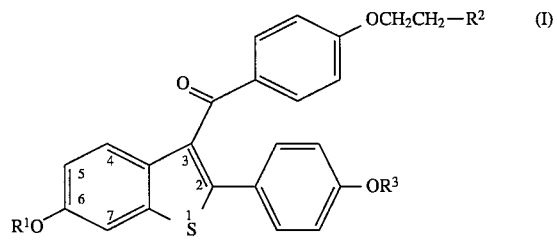

wherein $R^1$ and $R^3$ are independently hydrogen, —$CH_3$,

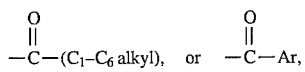

wherein Ar is optionally substituted phenyl;

$R^2$ is piperidino; or a pharmaceutically acceptable salt of solvate thereof.

2. The method of claim 1 wherein said compound is the hydrochloride salt thereof.

3. The method of claim 1 wherein said administration is prophylactic.

4. The method of claim 1 wherein said compound is

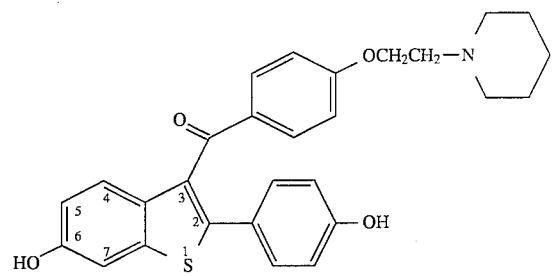

or its hydrochloride salt.

5. The method of claim 1 wherein said tissue is kidney, pulmonary tract, liver or vasculature tissue.

* * * * *